United States Patent [19]
Yoshioka

[11] Patent Number: 6,156,023
[45] Date of Patent: Dec. 5, 2000

[54] DISPOSABLE DIAPER

[75] Inventor: Toshiyasu Yoshioka, Kagawa-ken, Japan

[73] Assignee: Uni-Charm, Japan

[21] Appl. No.: 09/277,693

[22] Filed: Mar. 26, 1999

[30] Foreign Application Priority Data

Mar. 27, 1998 [JP] Japan .................................. 10-081139

[51] Int. Cl.[7] .................................................. A61F 13/15
[52] U.S. Cl. .......................................................... 604/385.2
[58] Field of Search ............................. 604/385.1, 385.2

[56] References Cited

U.S. PATENT DOCUMENTS

| | | | |
|---|---|---|---|
| 4,407,284 | 10/1983 | Pieniak | 604/385 |
| 5,342,342 | 8/1994 | Kitaoka | 604/285.2 |
| 5,403,301 | 4/1995 | Huffman et al. . | |
| 5,672,166 | 9/1997 | Vandemoortele | 604/385.2 |
| 5,685,874 | 11/1997 | Buell et al. | 604/396 |

FOREIGN PATENT DOCUMENTS 0321732  6/1989  European Pat. Off. .
0346477  12/1989  European Pat. Off. .
0648482  4/1995  European Pat. Off. .
3-80502  12/1991  Japan .

*Primary Examiner*—Wynn Wood Coggins
*Assistant Examiner*—Deborah Blyveis
*Attorney, Agent, or Firm*—Baker & Daniels

[57] ABSTRACT

A disposable diaper includes barrier cuffs around wearer's legs. Each of the barrier cuffs longitudinally extends on an inner surface of the disposable diaper and includes a supporting wall section adapted to rise on the inner surface of the diaper and a sealing surface zone which includes a first overhead section extending inwards from the supporting wall section and a second overhead section extending outwards from the supporting wall section. A first elastic member extending along an inner edge of the sealing surface zone in operative association with the first overhead section has an elongation stress higher than that of a second elastic member extending along an outer edge of the sealing surface zone in operative association with the second overhead section. The barrier cuffs thus constructed provide a good fit around a wearer's legs to prevent body fluids from leaking.

5 Claims, 3 Drawing Sheets

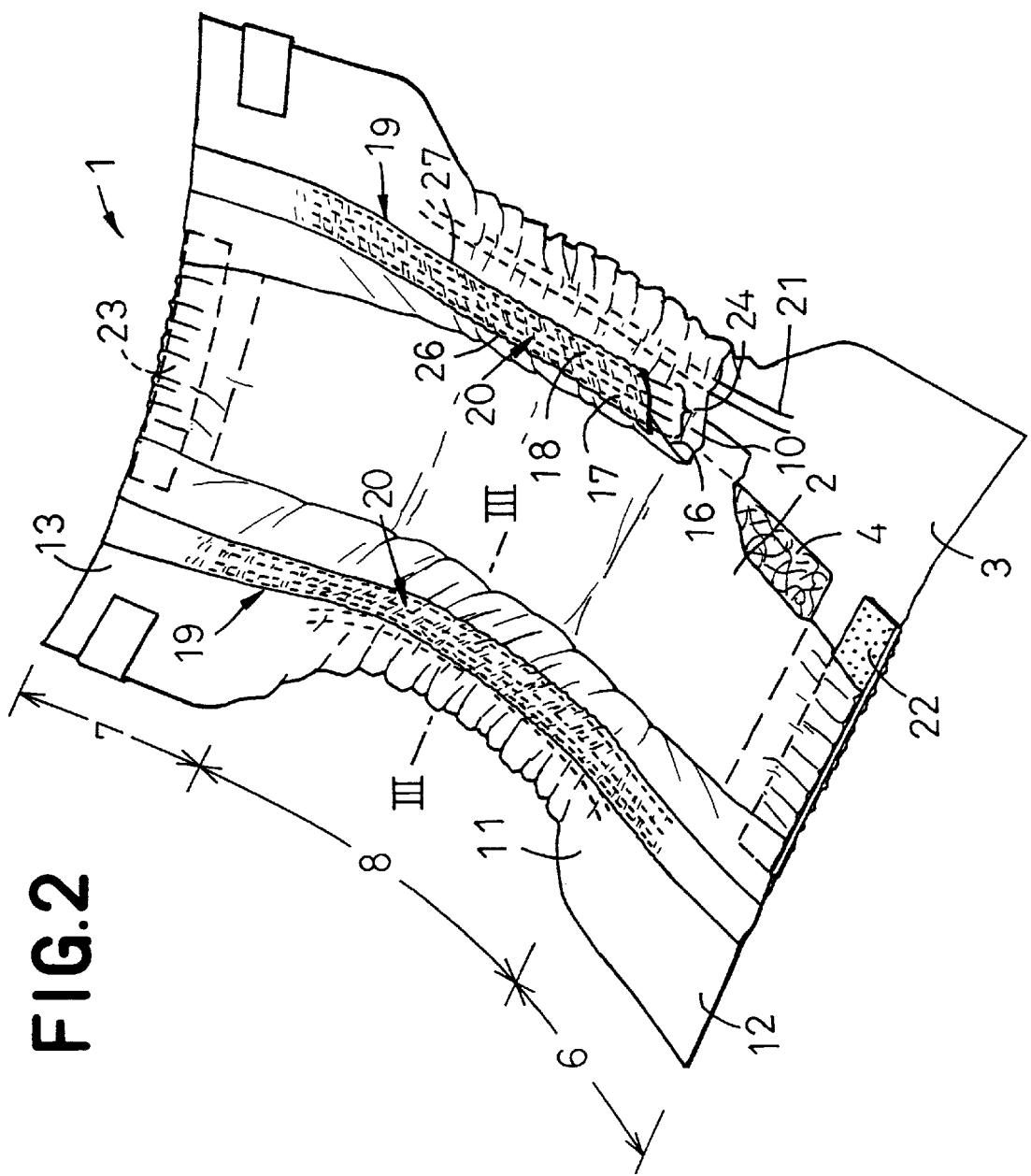

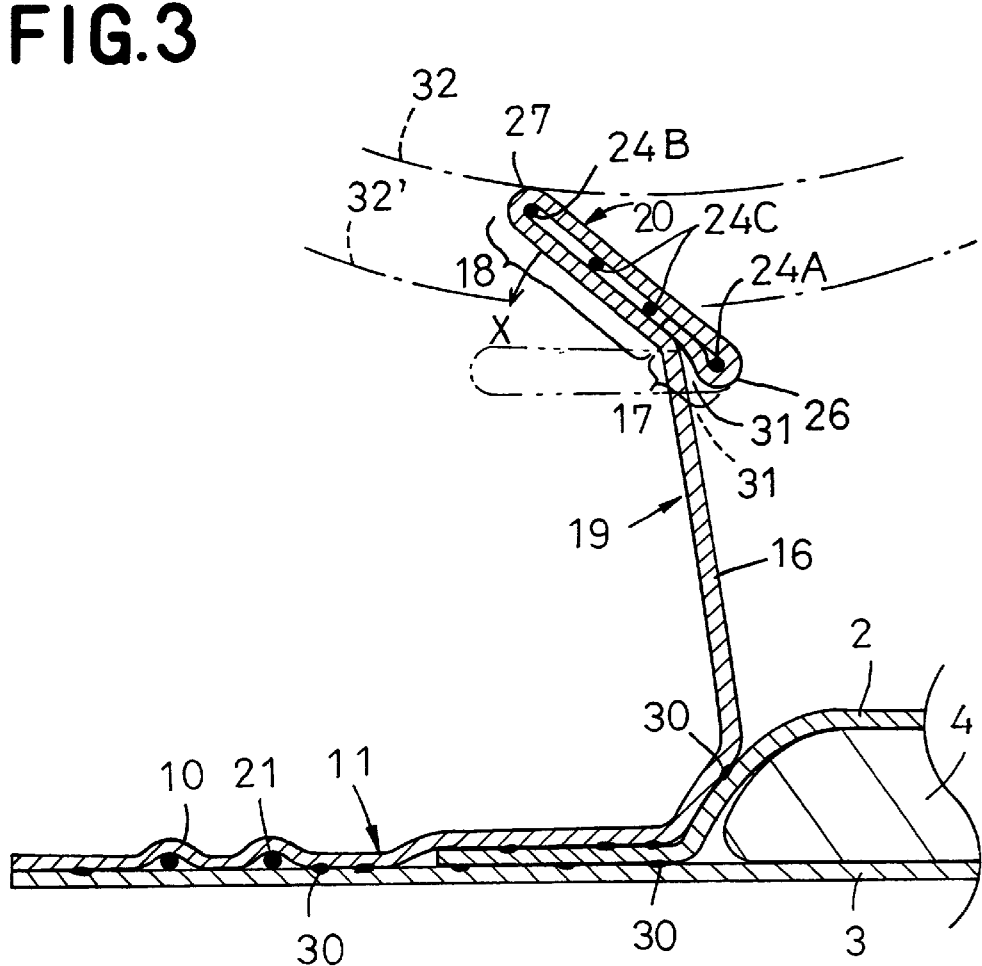

DISPOSABLE DIAPER

BACKGROUND OF THE INVENTION

This invention relates to a disposable diaper having barrier cuffs and the like.

Japanese Patent Publication No. Hei3-80502 discloses a disposable diaper comprising a liquid-pervious topsheet, a liquid-impervious backsheet, a liquid-absorbent core disposed between these two sheets and a pair of barrier cuffs in the form of flexible flaps adapted to be stretched and contracted under effect of elastic members. Each of the barrier cuffs comprises a branch section extending upwards from an inner surface of the diaper, and a sealing surface zone consisting of a first overhead section extending inwards from the branch section and a second overhead section extending outwards from the branch section. The elastic members are provided in the seal surface zone. With the diaper of such a well known arrangement, it can be principally expected that the first overhead section elastically fits around the wearer's thigh and thereby forms an inwardly opening pocket to receive loose passage or urine. The second overhead section also elastically fits around the wearer's thigh and improves a preventive effect against leakage of excretion.

SUMMARY OF THE INVENTION

For the well known diaper as has been described, it is desired that the first and second overhead sections can be laterally developed without being folded one upon another and come in contact with the wearer's thigh over an area as large as possible. In view of this demand, it is an object of the invention to improve the known diaper so that the first and second overhead sections can be reliably developed and brought in contact with the wearer's thigh in the desired manner.

According to the invention, there is provided a disposable diaper having a front waist region, a rear waist region and a crotch region therebetween, the diaper including a liquid-pervious topsheet, a liquid-impervious backsheet and a liquid-absorbent core disposed therebetween, and further including a pair of flexible barrier cuffs extending in a longitudinal direction along the crotch region into the front and rear waist regions and adapted to be elastically stretched/contracted in the direction under effect of a plurality of elastic members; each of the cuffs including a supporting wall section which extends from an inner surface of the diaper and a sealing surface zone which includes, in turn, a first overhead section extending inwards from the supporting wall section and a second overhead section extending outwards from the supporting wall section; wherein in the sealing surface zone, the elastic members extend in parallel one to another in the direction along the crotch region into the front and rear waist regions and are secured to the sealing surface zone under tension in the direction so that the elastic member lying along an inner edge of the sealing surface zone has an elongation stress higher than those of the remaining elastic members.

According to an embodiment of the invention, the first overhead section is provided along the inner edge of the sealing surface zone with one of the elastic members and the second overhead section is provided with two or more of the elastic members of which the one extends along the outer edge of the sealing surface zone and the remaining elastic member or members lies or lie between the outer edge and the supporting wall section in such a manner that the remaining elastic member or members has or have an elongation stress identical to or lower than that of the elastic member extending along the outer edge.

In the disposable diaper according to the invention, each of the barrier cuffs includes the supporting wall section risable on the side flap and the sealing surface zone lying on the top end of the supporting wall section. The elongation stress of the elastic members contained in the sealing surface zone is adjusted so that the elastic member lying extending along the inner edge may have the highest elongation stress and the elastic member lying extending along the outer edge may have the lowest elongation stress. By adjusting the elongation stress of the elastic members in this manner, the sealing surface zone swings outwards around the elastic member extending along the inner edge to fit around each of the wearer's legs over a large area and reliably prevents undesirable leakage of body fluids.

BRIEF DESCRIPTION OF THE DRAWINGS

FIG. 2 is a perspective view showing the diaper as somewhat curved as partially broken away; and FIG. 3 is a sectional view taken along line III—III in FIG. 2.

DETAILED DESCRIPTION OF THE PREFERRED EMBODIMENTS

Figure 1:
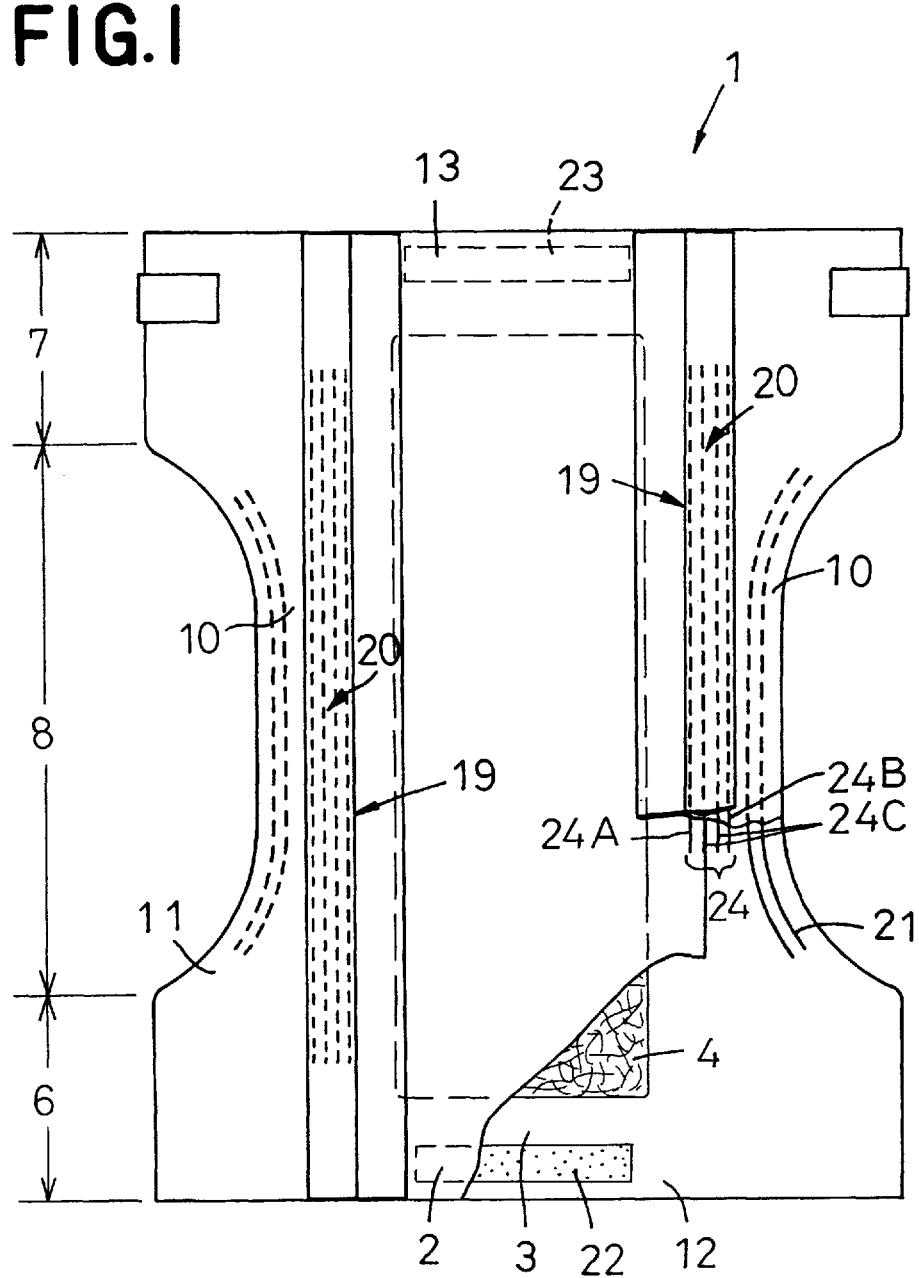
FIG. 1 is a plan view showing a disposable diaper constructed according to one embodiment of the invention as developed.

Details of a disposable diaper according to the invention will be more fully understood from the description of a preferred embodiment given hereunder with respect to the accompanying drawings.

FIG. 1 is a plan view showing a disposable diaper 1 as partially broken away and FIG. 2 is a perspective view of the diaper 1 as partially broken away. FIG. 2 shows the diaper 1 as somewhat curved due to contraction of respective elastic members as will be described later in more detail.

The diaper 1 includes a liquid-pervious topsheet 2, a liquid-impervious backsheet 3 and a liquid-absorbent core 4 disposed between these two sheets 2, 3. These elements define a front waist region 6, a rear waist region 7 and a crotch region 8 extending between the front and rear waist regions 6, 7. The topsheet 2 and the backsheet 3 extend outwards beyond peripheral edges of the absorbent core 4 and are joined together along these extensions to form a pair of transversely opposite side flaps 11, 11 and a pair of longitudinally opposite end flaps 12, 13. The respective side flaps 11, 11 are provided on their upper surfaces with barrier cuffs 19. Each of these barrier cuffs 19 comprises a proximal section 10 defining an upper surface of the side flap 11, a supporting wall section 16 extending upwardly of the diaper 1 from the proximal section 10, and a sealing surface zone 20 which includes, in turn, a first overhang section 17 extending inwardly of the supporting wall section 16 and a second overhang section 18 extending outwardly of said supporting wall section 16. The barrier cuff 19 longitudinally extends along the crotch region 8 into the front and rear waist regions 6, 7. Longitudinally opposite ends of the first and second overhang sections 17, 18, respectively, are joined to an inner surface of the diaper 1. In the crotch region 8, the side flap 11 is provided with a plurality of elastic members 21 extending longitudinally of the side flap 11 so as to be operatively associated with each leg-opening. These elastic members 21 are disposed between the topsheet 2 and the backsheet 3 or, as shown in FIG. 2, between the backsheet 3 and the proximal section 10 joined on an upper surface of the extension of the backsheet 3 and secured under appropriate tension between them. The end flaps 12, 13, on the other hand, are respectively provided with elastic members 22, 23 made of a foamed polyurethane sheet extending circumferentially of the diaper 1. These elastic members 22, 23 are intermittently secured with appropriate tension between the topsheet 2 and the backsheet 3. The sealing surface zone 20 contains a plurality of elastic members 24 extending longitudinally of the diaper 1 and secured under appropriate tension to the sealing surface zone 20.

FIG. 3 is a fragmentary sectional view of the diaper 1 taken along line III—III in FIG. 2. The elastic members 24 contained in the sealing surface zone 20 include a first elastic member 24A longitudinally extending in the first overhang section 17 along an inner edge 26 of the sealing surface zone 20, a second elastic member 24B longitudinally extending in the second overhang section 18 along an outer edge 27 of the sealing surface zone 20 and third elastic members 24C lying between the outer edge 27 and the supporting wall section 16. These third elastic members 24C also extend longitudinally of the sealing surface zone 20. While the first overhead section 17 is provided with the single elastic member 24A in the embodiment shown in FIG. 3, it is possible to provide a plurality of such elastic members 24A. In the case of FIG. 3, the first elastic member 24A lies adjacent a top end of the supporting wall section 16, preferably in a range of 0~3 mm, and more preferably in a range of 0.5~2 mm from the top end. With the diaper 1 developed longitudinally of the diaper 1 as seen in FIG. 1, the first and second elastic members 24A, 24B extend between longitudinally opposite ends of the first and second overhead sections 17, 18, respectively, substantially over an identical length. The first elastic member 24A preferably has an elongation stress higher than that of the second elastic member 24B, more preferably an elongation stress and an elongation percentage both higher than those of the second elastic member 24B. The third elastic members 24C have a length substantially identical to or shorter than those of the first and second elastic members 24A, 24B. The third elastic members 24C have an elongation stress identical to or lower than that of the second elastic member 24B and an elongation percentage identical to or higher than that of the second elastic member 24B.

The topsheet 2 and the backsheet 3 are joined together in a water-tight manner along their extensions outwards beyond the peripheral edge of the absorbent core 4 by means of hot melt adhesive 30. The backsheet 3 extends further outwards beyond transversely opposite side edges of the topsheet 2 and the proximal section 10 forming a part of the barrier cuff 19 is joined to the outward extension of the backsheet 3 preferably in a water-tight manner by means of hot melt adhesive 30. The proximal section 10 extends inwardly of the diaper 1 so as to be placed upon the topsheet 2 and joined thereto preferably in a water-tight manner by means of hot melt adhesive 30.

With the barrier cuff 19 constructed as has been described above, the first, second and third elastic members 24A~24C are stretched and placed against the inner surface of the diaper 1 as the diaper 1 is longitudinally developed (See FIG. 1). When the diaper 1 is longitudinally curved with the topsheet 2 inside, the first and second elastic members 24A, 24B predominantly contract due to their relatively high elongation stresses as well as elongation percentage (See FIG. 2) so that the supporting wall section 16 of the barrier cuff 19 rises on the side flap 11 and the sealing surface zone 20 is inclined towards the first overhead section 17 (See FIG. 3). The third elastic members 24C serve to prevent the sealing surface zone 20 from slackening between the first and second elastic members 24A, 24B. The first overhead section 17 cooperates with the supporting wall section 16 to form a pocket 31 opening downwards and inwardly of the diaper 1.

The outer edge 27 of the sealing surface section 20 as the important part of the risen barrier cuff 19 comes in contact with a wearer's leg indicated by imaginary lines as the diaper is put on the wearer's body. With the outer side edge 27 being more tightly placed around the wearer's leg, the sealing surface zone 20 swings in a direction indicated by an arrow X around the first elastic member 24A having the highest elongation stress and, as indicated by imaginary lines, is placed against the wearer's leg 32' over its circumferential area as large as possible, whereupon the pocket 31 is opened as largely as possible.

The diaper 1 of such arrangement enables the supporting wall section 16 to obstruct an amount of body fluids tending to flow laterally and thereby to prevent sideways leakage. An amount of body fluids flowing along the supporting wall section 16 to its top end is prevented by a lower surface of the first overhead section 17 from entering into a gap defined between the wearer's leg 32 or 32' and the sealing surface zone 20. Even if an amount of body fluids enters into the gap, it never happens that the amount of body fluids might easily arrive at the exterior of the diaper 1 since the barrier cuff 19 has the relatively large sealing surface zone 20 adapted to fit around the wearer's leg. Such effective function of the barrier cuff 19 allows the diaper 1 to be substantially free from leakage of body fluids.

The first overhead section 17 is not limited to the specific embodiment as has been described above. For example, it is also possible to provide a plurality of elastic elements 24 extending in parallel one to another. While these elastic members 24A may be identical in their length as well as elongation percentage and elongation stress, the elongation stress is preferably adjusted so that the elastic member 24A lying nearer the inner edge 26 of the sealing surface zone 20 may have correspondingly higher elongation stress. If it is not imperative to prevent the sealing surface zone 20 from slackening between its inner and outer edges 26, 27, the third elastic member 24C may be eliminated.

The supporting wall section 16 and the sealing surface zone 20 of the barrier cuff 19 are made of a nonwoven fabric or a plastic sheet, preferably of a liquid-impervious nonwoven fabric or a plastic sheet and more preferably of a breathable/liquid-impervious nonwoven fabric or a plastic sheet. The topsheet 2 may be made of a liquid-pervious nonwoven fabric or a apertured plastic sheet. The backsheet 3 may be made of a liquid-impervious plastic sheet and the absorbent core 4 may be made of fluff pulp or a mixture of fluff pulp and superabsorptive polymer particles. The respective elastic members of the diaper 1 may be secured to the sheet members by means of hot melt adhesive. The different sheets may be joined together by means of hot melt adhesive or use of heat-seal technique.

What is claimed is:

1. A disposable diaper having a front waist region, a rear waist region and a crotch region therebetween, said diaper including a liquid-pervious topsheet, a liquid-impervious backsheet and a liquid-absorbent core disposed therebetween, and further including a pair of flexible barrier cuffs extending in a longitudinal direction along said crotch region into said front and rear waist regions, said pair of flexible barrier cuffs being elastically stretchable/contractible in said longitudinal direction due to an effect caused by a provided plurality of elastic members; each of said pair of flexible barrier cuffs including a supporting wall section which extends upwardly from an inner surface of said diaper and a sealing surface zone which includes a first overhead section extending inwards from said supporting wall section and a second overhead section extending outwards from said supporting wall section;

wherein in said sealing surface zone, said plurality of elastic members extend in parallel one to another in said longitudinal direction along said crotch region into said front and rear waist regions and are secured to said sealing surface zone under tension in said longitudinal direction so that an elastic member lying along an inner edge of said sealing surface zone has an elongation stress higher than elongation stresses of the remaining ones of said plurality of elastic members.

2. A disposable diaper according to claim 1, wherein a first one of said plurality of elastic members is provided along the inner edge of said sealing surface zone of said first overhead section, a second one of said plurality of elastic member extends along an outer edge of said sealing surface zone of said second over head section, and remaining ones of said plurality of elastic members lie between said outer edge and said supporting wall section in such a manner that they have an elongation stress identical to or lower than an elongation stress of said second elastic member.

3. A disposable diaper according to claim 1, wherein each said pair of flexible barrier cuffs further includes a proximal section which forms an upper surface of a side flap extending outwardly of a transverse side edge of said absorbent core.

4. A disposable diaper according to claim 1, wherein the first overhead section has a width extending inwards from the supporting wall section that is greater than a width of the second overhead section that extends outwards from the supporting wall section.

5. A disposable diaper according to claim 1, wherein each of the flexible barrier cuffs is made from a single continuous sheet of material.

\* \* \* \* \*